US008311702B2

(12) United States Patent
Miki (10) Patent No.: US 8,311,702 B2
(45) Date of Patent: Nov. 13, 2012

(54) HEALTH STATE MANAGEMENT DEVICE AND HEALTH STATE MANAGEMENT SYSTEM

(75) Inventor: Masahiro Miki, Osaka (JP)

(73) Assignee: Laurel Machinery Co., Ltd., Osaka (JP)

( * ) Notice: Subject to any disclaimer, the term of this patent is extended or adjusted under 35 U.S.C. 154(b) by 721 days.

(21) Appl. No.: 12/353,526

(22) Filed: Jan. 14, 2009

(65) Prior Publication Data

US 2009/0187309 A1 Jul. 23, 2009

(30) Foreign Application Priority Data

Jan. 18, 2008 (JP) .................. P2008-009395

(51) Int. Cl.
*B60K 28/06* (2006.01)
(52) U.S. Cl. .......................... 701/36; 382/115
(58) Field of Classification Search .......... 701/36, 701/50; 180/272, 287; 340/576; 600/322, 600/316; 382/124, 115
See application file for complete search history.

(56) References Cited

U.S. PATENT DOCUMENTS

| | | | | | |
|---|---|---|---|---|---|
| 5,743,349 | A | * | 4/1998 | Steinberg | 180/272 |
| 6,229,908 | B1 | * | 5/2001 | Edmonds et al. | 382/124 |
| 6,961,581 | B2 | * | 11/2005 | Goto et al. | 455/522 |
| 7,413,047 | B2 | * | 8/2008 | Brown et al. | 180/272 |
| 2004/0240712 | A1 | * | 12/2004 | Rowe et al. | 382/124 |
| 2005/0087382 | A1 | * | 4/2005 | Bellehumeur | 180/272 |
| 2005/0099310 | A1 | * | 5/2005 | Jones | 340/576 |
| 2005/0192493 | A1 | * | 9/2005 | Wuori | 600/322 |
| 2006/0237251 | A1 | * | 10/2006 | LeBlanc Sr et al. | 180/252 |
| 2007/0168125 | A1 | | 7/2007 | Petrik | |
| 2007/0239992 | A1 | | 10/2007 | White et al. | |

FOREIGN PATENT DOCUMENTS

| | | |
|---|---|---|
| DE | 20 2005 020535 U1 | 4/2006 |
| EP | 1 995 107 A | 11/2008 |
| JP | 11-328593 | 11/1999 |
| JP | 2003-146107 | 5/2003 |
| JP | 2004-298572 | 10/2004 |
| JP | 2005-166064 | 6/2005 |
| JP | 2005166064 * | 6/2005 |
| JP | 2006-248254 | 9/2006 |
| JP | 2006248254 * | 9/2006 |
| JP | 2007-024543 | 2/2007 |

(Continued)

OTHER PUBLICATIONS

Official Action (and English translation) issued in KR 10-2009-0003062 issued Oct. 21, 2010.
Official Action (Notice of Allowance) with English translation in Korean Appln. 10-2009-0003062 dated Jan. 3, 2011.

(Continued)

*Primary Examiner* — Thomas Black
*Assistant Examiner* — Marthe Marc-Coleman
(74) *Attorney, Agent, or Firm* — Nixon & Vanderhye P.C.

(57) ABSTRACT

A health state management device manages information on a state of health of a driver of transportation equipment. An authentication portion authenticates the driver, and a health state judgment portion measures blood component data of the driver authenticated by the authentication portion. The health state judgment portion judges the state of health of the driver using the blood component data. A decision portion decides whether or not to permit operation of the transportation equipment based on a judgment result of the health state judgment portion, and a storage portion stores the judgment result of the health state judgment portion and a decision result of the decision portion in association with driver identification information of the driver.

11 Claims, 4 Drawing Sheets

FOREIGN PATENT DOCUMENTS

| | | | |
|---|---|---|---|
| JP | 2007-097820 | | 4/2007 |
| JP | 2007-217903 | | 8/2007 |
| JP | 2007217903 | * | 8/2007 |
| JP | 2008-086724 | | 4/2008 |
| KR | 10-2006-0052429 | | 5/2006 |
| TW | 200738504 | | 10/2007 |
| WO | WO 99/32317 A | | 7/1999 |

OTHER PUBLICATIONS

Office Action dated Dec. 23, 2011 issued in Taiwanese Patent Application No. 098100207 with translation, 9 pp.

Notice of Allowance dated Jun. 5, 2012 issued in Japanese Patent Application No. 2008-009395 with translation, 6 pp.

* cited by examiner

HEALTH STATE MANAGEMENT DEVICE AND HEALTH STATE MANAGEMENT SYSTEM

BACKGROUND OF THE INVENTION

1. Field of the Invention

The present invention relates to a health state management device and to a health state management system, which manages the state of health of a driver of an automobile or other vehicle, ship, aircraft, or other types of transportation equipment.

Priority is claimed on Japanese Patent Application No. 2008-009395, filed Jan. 18, 2008, the content of which is incorporated herein by reference.

2. Description of the Related Art

Japanese Unexamined Patent Application, First Publication No. 2006-248254discloses technology which authenticates a driver, and moreover measures the alcohol concentration contained in the breath of the driver, and, when the alcohol concentration is equal to or greater than a preset concentration, limits startup of the engines of automobiles owned by the driver via a network.

However, the above-described technology of the prior art detects only the alcohol concentration in the breath of the driver. Hence there is the problem that if no alcohol is detected, driving is permitted even in cases in which the state of health of the driver is not satisfactory, and it is undesirable that the driver be permitted to drive because judgment is impaired.

SUMMARY OF THE INVENTION

An object of the present invention is to provide a health state management device and a health state management system which are capable of deciding whether or not to permit operation of transportation equipment based on information on the state of health of the driver.

In order to attain the above object, the health state management device according to the present invention manages information on a state of health of a driver of transportation equipment, and includes: an authentication portion which authenticates the driver; a health state judgment portion which measures blood component data of the driver authenticated by the authentication portion, and which judges the state of health of the driver using the blood component data; a decision portion which decides whether or not to permit operation of the transportation equipment based on a judgment result of the health state judgment portion; and a storage portion which stores the judgment result of the health state judgment portion and a decision result of the decision portion in association with driver identification information of the driver.

By means of this configuration, the health state judgment portion measures the blood component data of a driver who has been authenticated by the authentication portion, and judges the state of health of the driver from the blood component data. Based on this judgment result, the decision portion decides whether to permit operation of the transportation equipment. Hence a decision as to whether to permit operation of transportation equipment can be made based on information on the state of health of the driver.

In the health state management device according to the present invention, the authentication portion may authenticate the driver by means of a vein pattern in a portion of a body of the driver.

By means of the above configuration, the authentication portion authenticates the driver using the vein pattern in a portion of the body of the driver, so that accurate authentication can be performed.

In the health state management device according to the present invention, the health state judgment portion may irradiate a portion of a body of the driver with infrared rays to obtain an absorption spectrum and may analyze the absorption spectrum to measure blood component data.

By means of the above configuration, the health state judgment portion irradiates a portion of a body of the driver with infrared rays to obtain an absorption spectrum, and analyzes the absorption spectrum. In this manner, the blood component data is obtained by a non-invasive method. Hence physical and metal stress on the driver can be reduced.

In the health state management device according to the present invention, the authentication portion may authenticate the driver by means of a vein pattern in a portion of a body of the driver, the health state judgment portion may irradiate a portion of a body of the driver with infrared rays to obtain an absorption spectrum and may analyze the absorption spectrum to measure blood component data, and detection of the vein pattern used by the authentication portion and acquisition of the absorption spectrum used by the health state judgment portion may be realized by means of a single sensor portion.

By means of the above configuration, detection of the vein pattern used by the authentication portion, and acquisition of the absorption spectrum used by the health state judgment portion, are realized by a single sensor portion. Hence authentication of the driver and judgment of the state of health are performed by the same operation, and the configuration of the system as a whole can be simplified.

In the health state management device according to present invention, the decision portion may permit operation of the transportation equipment when values of all items of the blood component data are within prescribed ranges determined for each of the items.

By means of the above configuration, when the values of all the items of the blood component data are within prescribed ranges determined for each item, the decision portion decides to permit operation of transportation equipment. Hence still more detailed information on the state of health of the driver can be obtained, and based on this information, a still more appropriate decision as to whether to permit operation of transportation equipment can be made.

In the health state management device according to present invention, the decision portion may decide not to permit operation of the transportation equipment when a value of a predetermined specific item among items of the blood component data is not within a prescribed range.

By means of the above configuration, when the value of a specific predetermined item among the items of the blood component data is not within the prescribed range, the decision portion decides not to permit operation of transportation equipment. Hence the decision as to whether to permit operation of transportation equipment can be made more appropriately.

In the health state management device according to the present invention, the decision portion may decide not to permit operation of the transportation equipment when number of items, other than the specific item, of the blood component data which are within prescribed ranges determined for each of the items is smaller than a prescribed number.

By means of the above configuration, when the number of items other than the specific items which are within the prescribed ranges is smaller than a prescribed number, the decision portion decides not to permit operation of the transportation equipment. Hence the decision as to whether to permit operation of transportation equipment can be made more appropriately.

The health state management device according to the present invention may her include an output portion which outputs the decision result of the decision portion.

By means of the above configuration, the decision result of the decision portion is output by the output portion, and so can be visually confirmed with reliability by the driver.

The health state management device according to the present invention may further include: a key management portion which accommodates and manages a key to the transportation equipment; and a control portion which, when operation of the transportation equipment is permitted by the decision portion, executes control to enable withdrawal of the key, accommodated by the key management portion, to the transportation equipment which can be operated by the driver, based on the driver identification information of the driver for whom the operation is permitted.

By means of the above configuration, when operation of transportation equipment has been permitted by the decision portion, the control portion executes control to enable withdrawal of the key, accommodated by the key management portion, to transportation equipment which can be operated by the driver, based on the driver identification information of the driver. Hence only the key to transportation equipment which can be operated by the driver is withdrawn.

The health state management system according to a first aspect of the present invention includes: the health state management device described above; a plurality of key managers which accommodate and manage keys including the key to the transportation equipment and which are connectable via a network to the health state management device; and a control portion which, when operation of the transportation equipment is permitted by the decision portion, executes control to enable withdrawal of the key, accommodated by the key managers, to transportation equipment which can be operated by the driver, based on the driver identification information of the driver for whom the operation is permitted.

By means of the above configuration, in the health state management device, the health state judgment portion measures blood component data for a driver who has been authenticated by the authentication portion, and judges the state of health of the driver from the blood component data. Based on the judgment result, the decision portion decides whether to permit operation of transportation equipment. Hence it is possible to decide whether to permit operation of transportation equipment based on information on the state of health of the driver. Moreover, in cases in which operation of transportation equipment has been permitted by the decision portion of the health state management device, the control portion executes control to enable withdrawal of the key, accommodated by the key managers which are connectable via a network to the health state management device, to transportation equipment which can be operated by the driver, based on the driver identification information for the driver. Hence only the key to transportation equipment which can be operated by the driver is withdrawn.

The health state management system according to a second aspect of the present invention includes: the health state management device described above; the transportation equipment which receives prescribed data from an IC chip held in a holder; a data writing portion which writes information on the decision result of the decision portion to the IC chip; a data reading portion which reads the information on the decision result of the decision portion written to the IC chip; and an engine control portion which executes control to enable starting of an engine of the transportation equipment when the information on the decision result read by the data reading portion is permission information which grants permission to operate the transportation equipment.

By means of the above configuration, in the health state management system, the health state judgment portion measures blood component data for a driver who has been authenticated by the authentication portion, and judges the state of health of the driver from the blood component data. Based on the judgment result, the decision portion decides whether to permit operation of transportation equipment. Hence it is possible to decide whether to permit operation of transportation equipment based on information on the state of health of the driver. Moreover, information on the decision result of the decision portion of the health state management device is written to the IC chip held in the holder by the data writing portion. The information on the decision result of the decision portion, written to the IC chip, is read by the data reading portion. When the decision result information thus read is permission decision granting permission to operate transportation equipment, the engine control portion executes control to enable starting of the engine of the transportation equipment. Hence the engine can be started only when a holder holding an IC chip which stores permission information granting permission to operate transportation equipment is read by the data reading portion.

DETAILED DESCRIPTION OF THE INVENTION

A health state management device according to a first embodiment of the invention is explained below with reference to FIG. 1.

Figure 1:
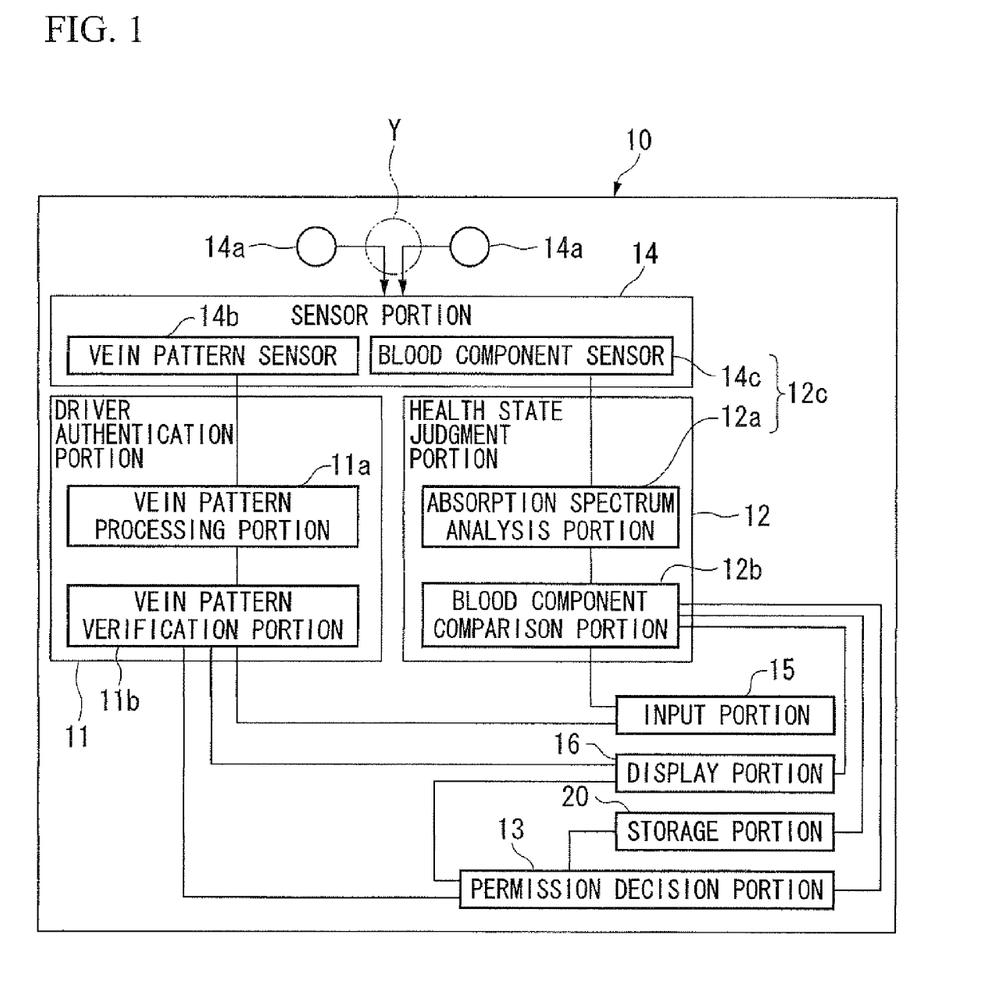
FIG. 1 is a block diagram showing a configuration of a health state management device according to a first embodiment of the invention.

The health state management device 10 shown in FIG. 1 measures the state of health of a driver (operator) of a truck, bus, taxi, railroad car, or other vehicle, or of a ship, aircraft, or other transportation equipment used for commercial purposes in particular, and manages this health state information. The health state management device 10 authenticates a driver as the previously registered, legitimate driver, judges the state of health thereof, and based on the judgment result, decides whether to permit operation (driving) of transportation equipment by the driver. The health state management device 10 stores, in association with driver identification information for the driver, the above-described health state judgment result and the result of the decision as to whether to permit operation, and in addition outputs the result of the decision as to whether to permit operation so as to enable visual confirmation by the driver.

The health state management device 10 includes a driver authentication portion (authentication portion) 11, health state judgment portion 12, permission decision portion (decision portion) 13, storage portion 20, and display portion (output portion) 16. The driver authentication portion 11 authenticates the driver as the legitimate driver. The health state judgment portion 12 measures blood component data of the driver being judged, who has been authenticated as the legitimate driver by the driver authentication portion 11, and moreover judges the state of health of the driver being judged from this blood component data. The permission decision portion 13 decides whether to permit operation of transportation equipment by the driver being judged, based on the judgment result of the health state judgment portion 12. The storage portion 20 stores, in association with driver identification information for the driver being judged, the judgment result of the health state judgment portion 12 and the decision result of the permission decision portion 13. The display portion 16 is a LCD (Liquid Crystal Display) or similar which outputs the result of the decision as to whether to permit operation by the driver being judged so as to enable visual confirmation.

The driver authentication portion 11 is a well-known vein authentication device. The driver authentication portion 11 acquires the vein pattern of a portion of the body of the driver, such as for example a fingertip, and verifies this vein pattern against the previously registered vein pattern of the legitimate driver. Based on the verification result, the driver authentication portion 11 judges whether the individual is an individual who has permitted to be a driver, that is, a legitimate driver. The vein pattern is acquired in the following manner. The driver holds his finger Y over a sensor portion (authentication portion, health state judgment portion) 14. This finger Y is irradiated with near-infrared light by an infrared LED 14a, and the transmitted light or the reflected light is received by a CCD (Charge Coupled Device) or other imaging element.

The sensor portion 14 has a vein pattern sensor 14b including this imaging element. The driver authentication portion 11 has a vein pattern processing portion 11a which performs prescribed image processing of signals from this vein pattern sensor 14b. The driver authentication portion 11 has a vein pattern verification portion 11b. Based on driver identification information input from an input portion 15, this vein pattern verification portion 11b reads the vein pattern of the driver, registered in advance, corresponding to the driver identification information. The input portion 15 is a keyboard, card reader, or similar.

The vein pattern verification portion 11b verifies the read-out vein pattern against the vein pattern acquired by the sensor portion 14 and image-processed by the vein pattern processing portion 11a. If the vein pattern verification portion 11b judges that the two vein patterns are the same, then the driver is authenticated as the legitimate driver. If on the other hand the vein pattern verification portion 11b judges that the two vein patterns are not the same, then the driver is not authenticated as the legitimate driver. The authentication result is displayed to the driver on the display portion 16. A configuration may also be employed in which input of driver identification information by the input portion 15 is eliminated, and the vein pattern acquired by the sensor portion 14 is verified separately and automatically against registered vein patterns to identify the driver identification information of the driver and perform authentication.

As the health state judgment portion 12, a well-known non-invasive blood component measurement device is used. The health state judgment portion 12 analyzes the absorption spectrum from transmitted light or reflected light resulting from irradiation with near-infrared rays to the finger Y of the driver being judged by the infrared LED 14a of the same sensor portion 14 as described above. From the analysis results of this absorption spectrum, the health state management portion 12 acquires data relating to blood components (blood component data) of the driver being judged. The health state judgment portion 12 has an absorption spectrum analysis portion 12a, which performs analysis of absorption spectra for the data of transmitted or reflected light resulting from the near-infrared light which irradiates the finger Y of the driver from the infrared LED 14a. This data has been acquired by the blood component sensor 14c. The blood component measurement portion 12c in the health state judgment portion 12 includes this absorption spectrum analysis portion 12a and the blood component sensor 14c of the sensor portion 14.

The blood component measurement portion 12c applies an infrared spectral photometer.

Items of blood components measured by the health state management portion 12 are blood sugar values, GPT (Glutamic Pyruvic Transaminase) and other enzyme values, albumin and other plasma protein values, as well as cholesterol values, lactic acid values, and similar.

The blood component comparison portion 12b of the health state judgment portion 12 reads prescribed tolerance ranges of blood component data, registered in advance for each item, indicating a state of health appropriate for operation.

The blood component comparison portion 12b compares, for each item, the tolerance ranges for each item of the read-out blood component data with experimental values of each item of the blood component data acquired from absorption spectrum analysis. From the several comparison results, the blood component comparison portion 12b judges whether the driver being judged is in a state of health appropriate for operation of transportation equipment.

Specifically, the blood component comparison portion 12b determines in advance, as special items among the blood component data items, the plasma protein value and lactic acid value as indicating the extent of fatigue of the driver. The blood component comparison portion 12b judges whether the values of these specific items in the measured blood component data are within the read-out blood component data values, that is, within the tolerance ranges determined in advance for each item. These tolerance ranges are ranges within which the state of health of the driver can be judged to be appropriate for operating transportation equipment. The tolerance ranges are set appropriately based on the age and sex of the driver as well as on individual differences. A configuration may be employed in which tolerance ranges are corrected or updated appropriately based on blood component data acquired in the past.

When the above-described specific item values are all within the respectively set tolerance ranges (when the specific items all satisfy requirements), the blood component comparison portion 12b judges the state of health of the driver being judged to be appropriate for operation of transportation equipment. If on the other hand at least one of the values of the above-described specific items is outside the tolerance range (if at least one requirement is not satisfied), the blood component comparison portion 12b judges the state of health of the driver being judged to be not appropriate for operation of transportation equipment.

When the number of items among all the items other than the above-described specific items which are within the respective preset tolerance ranges is equal to or greater than a prescribed number (for example, half), the blood component comparison portion 12b judges the state of health of the driver being judged to be appropriate for operation of transportation equipment. If on the other hand the number of items among all the items other than the above-described specific items which are within the respective preset tolerance ranges is less than the prescribed number, then the blood component comparison portion 12*b* judges the state of health of the driver being judged to be not appropriate for operation of transportation equipment.

When, in both judgment results for specific items of blood component data and in judgment results for items other than specific items, the state of health of the driver being judged is judged to a state appropriate for operation of transportation equipment, the permission decision portion 13 decides to permit operation of transportation equipment by the driver being judged. If, on the other hand, in at least one or the other of the judgments, the state of health of the driver being judged is judged to be a state not appropriate for operation of transportation equipment, the permission decision portion 13 decides not to permit operation of transportation equipment by the driver being judged.

The permission decision portion 13 may also perform decisions as to whether to permit operation of transportation equipment as follows. The permission decision portion 13 does not set specific items, and only when all of the items of the blood component data are within the respectively set tolerance ranges the permission decision portion 13 decides to permit operation of transportation equipment by the driver being judged. On the other hand, when at least one item is not within the tolerance range, then the permission decision portion 13 decides operation of transportation equipment by the driver being judged is not permitted. Otherwise, when a prescribed number or greater among all the items of the blood component data are within the respectively set tolerance ranges, the permission decision portion 13 decides to permit operation of transportation equipment by the driver being judged. On the other hand, when the number of items within the tolerance ranges among all the items of the blood component data is less than a prescribed number, the permission decision portion 13 decides not to permit operation of transportation equipment by the driver being judged. Moreover, a configuration may be employed in which the user can select and set any one of the above-described decision methods.

The permission decision portion 13 causes the display portion 16 to display the above-described decision result in association with the driver identification information for the driver being judged. That is, when a decision is made to permit operation of transportation equipment by the driver being judged, the permission decision portion 13 causes the massage saying "Operation by driver A is permitted" to be displayed on the display portion 16. If on the other hand the permission decision portion 13 decides not to permit operation of transportation equipment by the driver being judged, the massage saying "Operation by driver A is not permitted" is caused to be displayed on the display portion 16.

The permission decision portion 13 stores in the storage portion 20 as log information, in association with the measurement date and driver identification information for the driver being judged who is the subject of the decision result, the result of the decision as to whether to permit operation of transportation equipment, the judgment result by the health state judgment portion 12 which is the basis for the decision result, and comparison results for all items of the blood component data. The log information stored in this storage portion 20 can be displayed as necessary on the display portion 16, or can be printed by means of a printer (output portion), not shown. This log information may be presented as numerical values, or may be displayed as a graph or similar. By storing such information as log information, the state of health on different days of each of the drivers can be reviewed.

By means of the first embodiment described above, the sensor portion 14 and health state judgment portion 12 measure blood component data for a driver being judged, who has been authenticated by the sensor portion 14 and driver authentication portion 11, and moreover judge the state of health of the driver being judged from the blood component data. Based on this judgment result, the permission decision portion 13 decides whether to permit operation of transportation equipment by the driver being judged. Hence a decision as to whether to permit operation of transportation equipment can be made based on information on the state of health of the driver being judged.

Further, the sensor portion 14 and the driver authentication portion 11 perform authentication of the driver being judged using the vein pattern of a portion of the body. Hence accurate authentication of the driver being judged can be performed.

Further, the sensor portion 14 and health state judgment portion 12 irradiate a portion of a body of the driver being judged with infrared rays to obtain an absorption spectrum and analyze the absorption spectrum to measure blood component data. In this manner, a non-invasive method is used to measure blood component data measurement, physical and metal stress on the driver being judged can be reduced.

Further, vein pattern detection used in the driver authentication portion 11, and absorption spectrum acquisition used in the health state judgment portion 12, can be realized by a single sensor portion 14. Hence authentication of the driver being judged and judgment of the state of health can be performed in the same operation, and the configuration of the system as a whole can be simplified.

Further, when the value of a specific item preset in advance among the items of the blood component data is not within the prescribed range, the permission decision portion 13 decides that operation of transpiration equipment is not permitted. Hence the decision as to whether to permit operation of transmission equipment can be made more appropriately.

Further, when the number of items other than specific items which are within prescribed ranges is less than a prescribed number, the permission decision portion 13 decides not to permit operation of transportation equipment. Hence the decision as to whether to permit operation of transportation equipment can be made more appropriately.

Further, by causing the decision result of the permission decision portion 13 to be output by the display portion 16, the result can be reliably presented for visual confirmation by the driver being judged.

When the values of all the items of blood component data are within the prescribed ranges determined for each item, if the permission decision portion 13 decides to permit operation of transportation equipment, still more detailed information on the state of health of the driver can be obtained. Based on this information, a decision as to whether to permit operation of transportation equipment can be made still more appropriately.

A health state management device according to a second embodiment of the invention is explained below, centering on differences from the health state management device according to the first embodiment with reference to FIG. 2.

Figure 2:
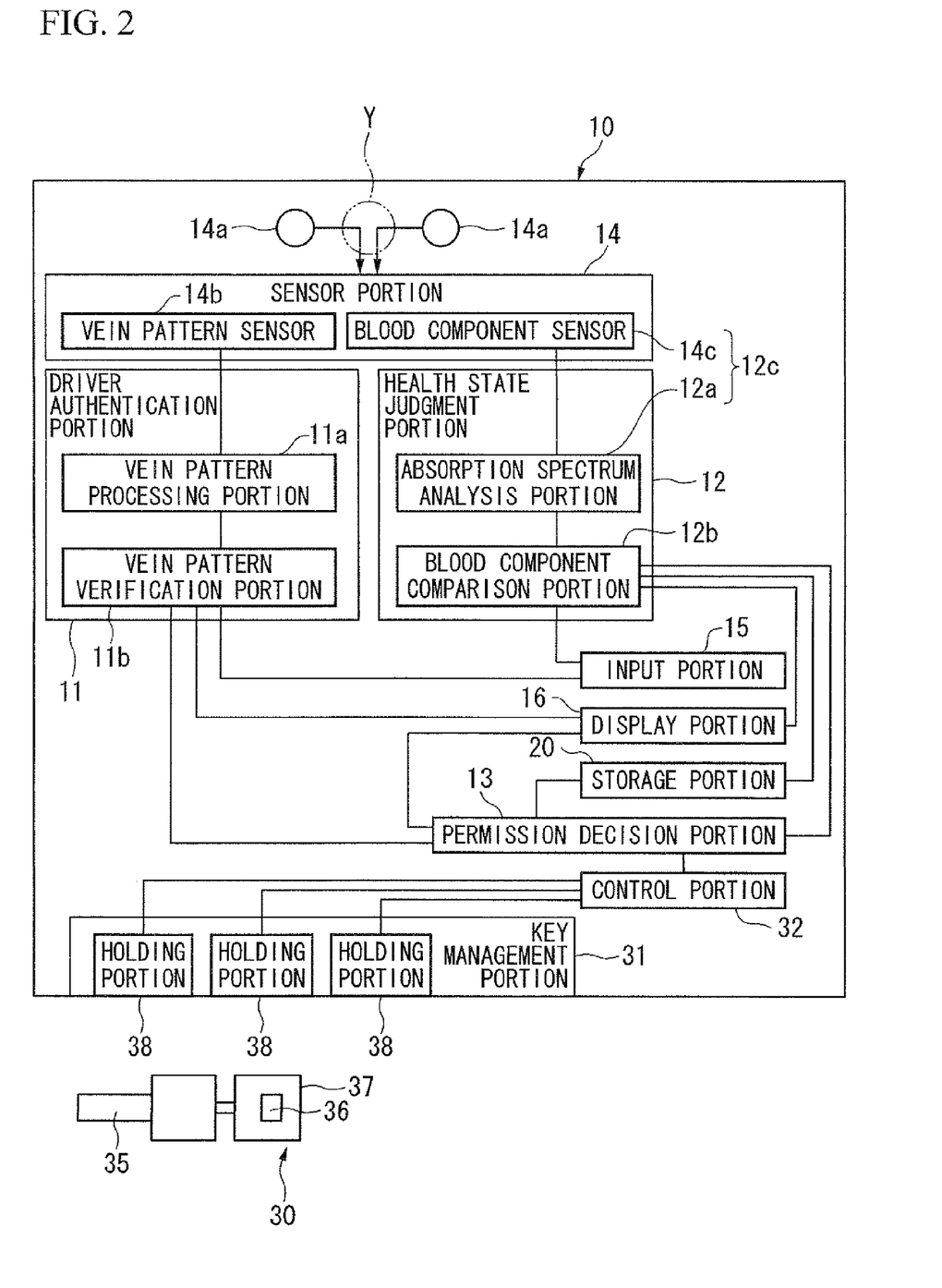
FIG. 2 is a block diagram showing a configuration of a health state management device according to a second embodiment of the invention.

The health state management device 10 shown in FIG. 2 includes a key management portion 31 and a control portion 32. The key management portion 31 accommodates and manages keys 30 to transportation equipment. When a decision has been made by the permission decision portion 13 to permit operation of transportation equipment by the driver being judged, the control portion 32 executes control so as to enable withdrawal of only the key 30 to transportation equipment which can be operated by the driver being judged, among the keys 30 accommodated in the key management portion 31, based on driver identification information from the driver authentication portion 11 for the driver being judged.

A key 30 includes a key body 35 and a key holder 37. The key holder 37 has an RFID (radio-frequency identification) IC chip 36 which stores key identification information, and displays key identification information which can be visually confirmed. The key management portion 31 is provided with holding portions 38 each of which can only hold the key holder 37 of the key 30 corresponding one-to-one and which can be individually locked and unlocked. On each holding portion 38 is displayed visually confirmable holding portion identification information. A driver inserts the key holder 37 of a key 30 into the holding portion 38 having holding portion identification information matching the key identification information displayed on the key holder 37. When a key holder 37 is inserted in this way, the holding portion 38 communicates with the IC chip 36 of the key holder 37 and reads the key identification information. The holding portion 38 locks the key holder 37 only in a case in which key identification information in a one-to-one correspondence is read from the IC chip 36. On the other hand, when the key holder 37 of a key 30 with key identification information that does not match is inserted, the key holder is not held, and instead a warning is issued and the driver is notified that the holding position is incorrect.

The holding portions 38 hold keys 30 which can be used by the driver identification information of drivers. Holding portion identification information for the holding portions 38 is stored in advance in the control portion 32. Similarly to the health state management device according to the first embodiment, when a decision is made to permit operation of transportation equipment by the permission decision portion 13 for a driver being judged, the control portion 32 unlocks a holding portion 38 having stored holding portion identification information which corresponds to the driver identification information of this driver being judged. On the other hand, the control portion 32 does not unlock holding portions 38 having other holding portion identification information. By this means, only the key 30 to transportation equipment which can be operated by the driver being judged can be withdrawn from the key management portion 31. On the other hand, when the permission decision portion 13 does not decide to permit operation of transportation equipment by the driver being judged, the control portion 32 does not unlock any of the holding portions 38.

Keys 30 may also be managed without providing IC chips 36 in key holders 37, using only visually confirmable holding portion identification information of holding portions 38 and visually confirmable key identification information of key holders 37. In this case, when a key 30 is returned, the driver inputs to the input portion 15 of the health state management device 10 information indicating that the key 30 is to be accommodated as well as the key identification number, and inserts the key holder 37 into the holding portion 38 having the corresponding key identification information. Then, the holding portion 38 locks the key holder 37, and stores information indicating that the key 30 with the key identification number input to the input portion 15 is held in the holding portion 38. On the other hand, if at the above-described time of return the key identification information for the key 30 which has been input to the input portion 15 is the key identification information for a key already held in a holding portion 38, an input error is detected and an alarm occurs.

By means of the above-described second embodiment, when the permission decision portion 13 permits operation of transportation equipment, the control portion 32 executes control to enable withdrawal of only a key 30 to transportation equipment which can be operated by the driver being judged, and which is accommodated in the key management portion 31, based on driver identification information for the driver being judged and who has been granted permission for operation. By this means, only a key 30 to transportation equipment which can be operated is withdrawn.

A health state management system according to a third embodiment of the invention is explained below, centering on differences with the health state management device according to the second embodiment with reference to FIG. 3.

Figure 3:
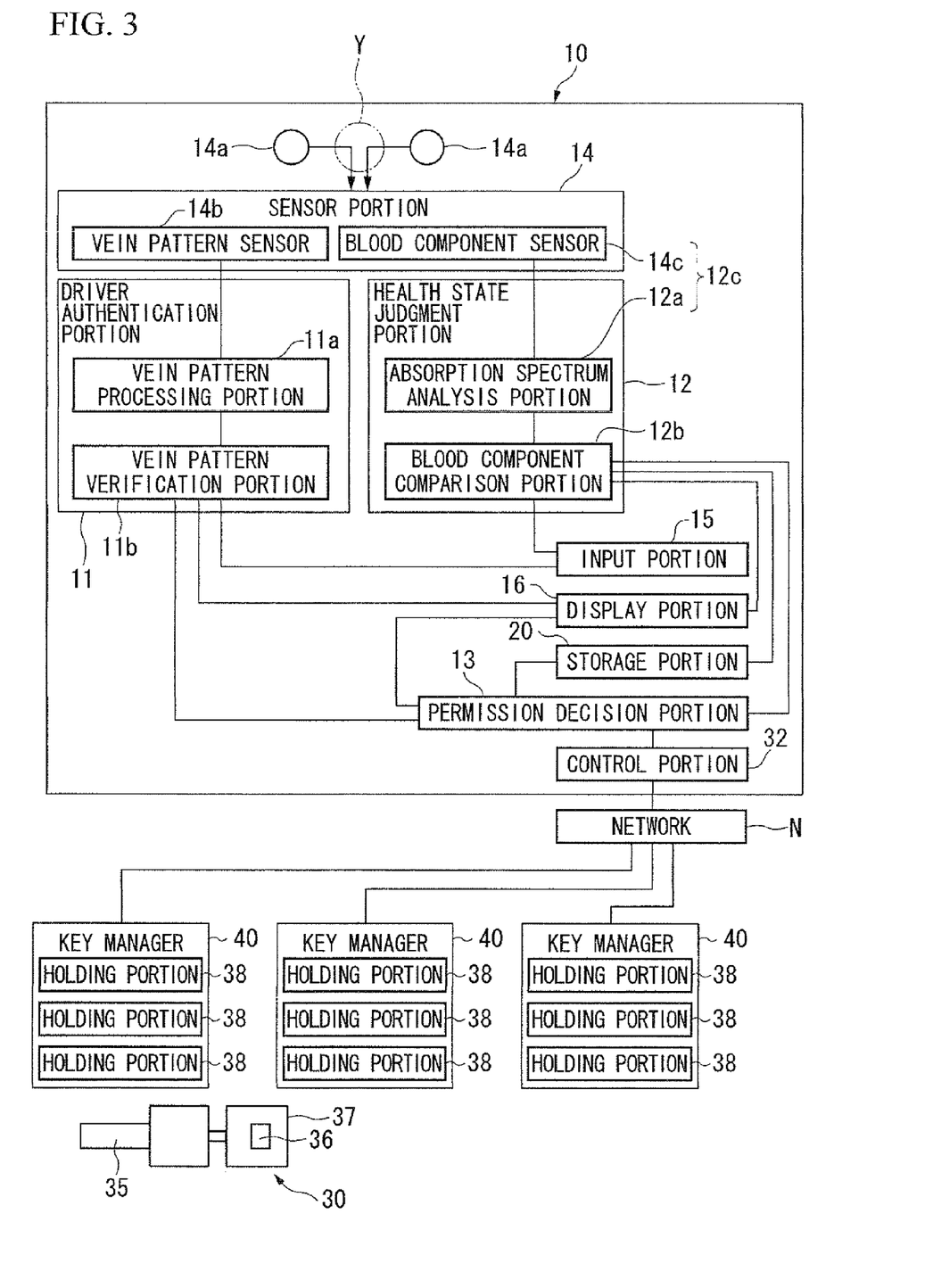
FIG. 3 is a block diagram showing a configuration of a health state management system according to a third embodiment of the invention.

As shown in FIG. 3, the health state management system 41 according the third embodiment is configured with a plurality of key managers 40, with configurations similar to that of the key management portion 31 described above, separate from the health state management device 10, connectable to the health state management device 10 via a wire or wireless network N.

The control portion 32 of the health state management device 10 stores in advance holding portion identification information for holding portions 38, including identification information for key managers 40, for the driver identification information of each driver. Similarly to the health state management device of the first embodiment, when the permission decision portion 13 makes a decision to permit operation of transportation equipment by a driver being judged, the control portion 32 puts into an unlockable state the holding portions 38 of the key manager 40 having stored holding portion identification information corresponding to the driver identification information of the driver being judged. However, at this time, the control portion 32 does not actually release the lock. When the driver being judged inputs appropriate driver identification information into this key manager 40, the key manager 40 unlocks the holding portion 38, corresponding to the input driver identification information, which had been in the unlockable state. By this means, only the key 30 to transportation equipment which can be operated by the driver being judged, for whom a decision to permit operation of the transportation equipment has been made, can be withdrawn. On the other hand, when the permission decision portion 13 does not make a decision to permit operation of transportation equipment by the driver being judged, the control portion 32 does not unlock the holding portions of any of the key managers 40.

By means of this third embodiment when the permission decision portion 13 of the health state management device 10 permits operation of transportation equipment by a driver being judged, the control portion 32 of the health state management device 10 executes control so as to enable withdrawal only of the key 30 to transportation equipment which can be operated by the driver being judged, and which is accommodated in a key manager 40 connectable via a network to the health state management device 10, based on identification information of this driver being judged. Hence only the key 30 to transportation equipment which can be operated is withdrawn.

A health state management system according to a fourth embodiment of the invention is explained below, centering on differences with the health state management device according to the first embodiment with reference to FIG. 4.

Figure 4:
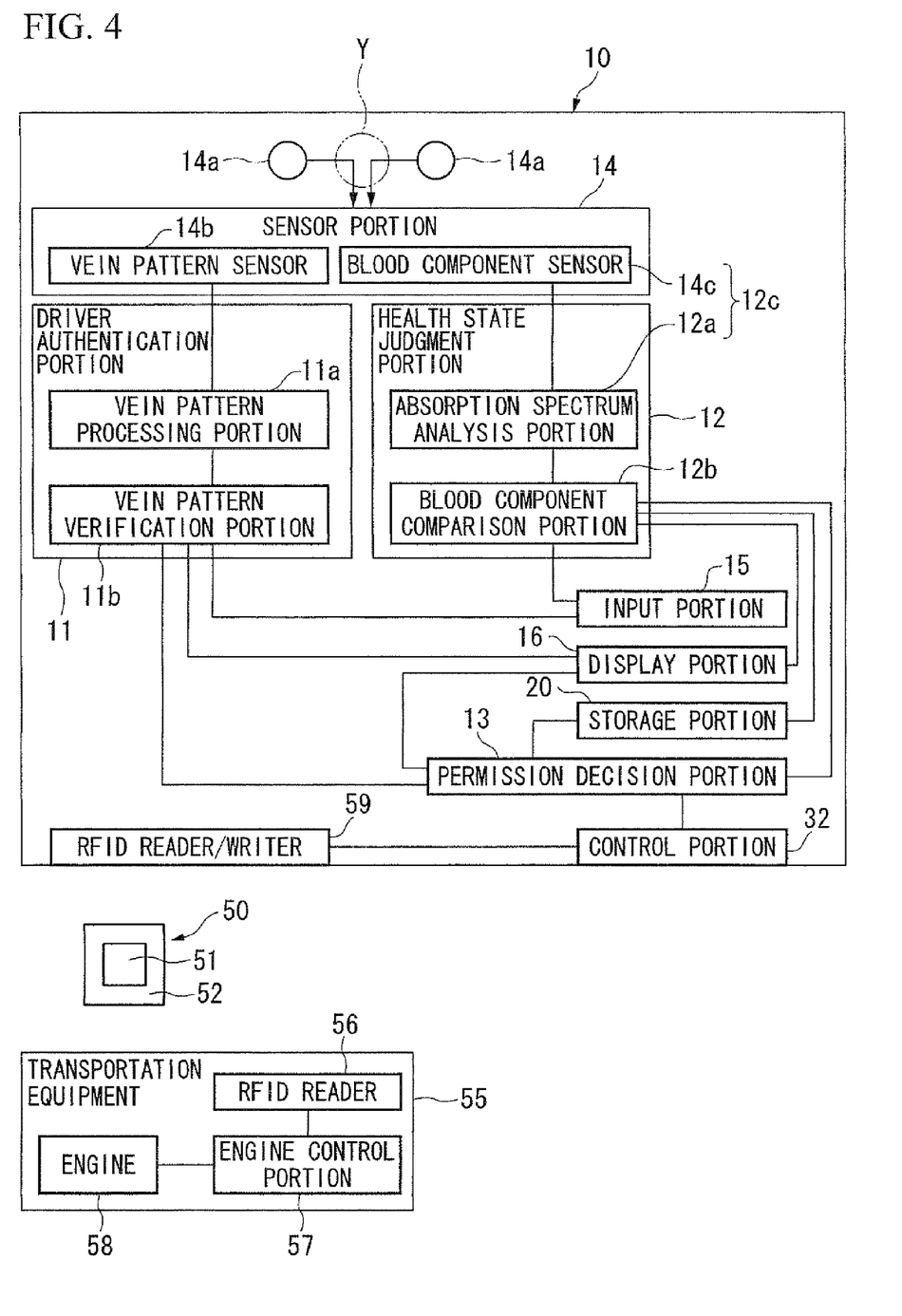
FIG. 4 is a block diagram showing a configuration of a health state management system according to a fourth embodiment of the invention.

As shown in FIG. 4, the health state management system according to the fourth embodiment has an ignition key 50, separate from the transportation equipment, which is necessary when starting the transportation equipment, and transportation equipment 55. This ignition key 50 is configured by embedding an RFID IC chip 51 in a holder 52, and is for example a card-type so-called smart key. The transportation equipment 55 is provided with an REID reader (data reading portion) 56, engine 58, and engine control portion 57 which controls the engine 58 of the transportation equipment 55. The RFID reader (data reading portion) 56 drives the IC chip 51 of the ignition key 50, and wirelessly receives information from the IC chip 51. The engine control portion 57 reads key identification information of the ignition key 50 from the IC chip 51, and enables starting of the engine only when this key identification information matches key identification information stored in advance.

The health state management device 10 is provided with an RFID reader/writer (data writing portion) 59, which can wirelessly write and delete information in the IC chip 51 of the ignition key 50.

The health state management system 60 according to the fourth embodiment includes an ignition key 50, health state management device 10 which writes information to the IC chip 51, and transportation equipment 55 which receives prescribed data from the health state management device 10 via the IC chip 51 of the ignition key 50.

In the health state management device 10, similarly to the first embodiment, when the permission decision portion 13 decides to permit operation of the transportation equipment 55 by a driver being judged, upon insertion of the ignition key 50 into the RFID reader/writer 59, the permission decision portion 13 uses the RFID reader/writer 59 to store, in the IC chip 51 of the ignition key 50, permission information indicating the decision to permit operation of the transportation equipment 55, and date-and-time information for the decision, calculated from an internal clock.

When the driver takes the ignition key 50, boards the corresponding transportation equipment 55, and performs the operation to start the engine 58, the RFID reader 56 of the transportation equipment 55 reads information from the IC chip 51 of the ignition key 50. The engine control portion 57 executes control to enable starting of the engine only when the key identification information of the ignition key 50 matches the key identification information stored in advance in the engine control portion 57, and moreover when the permission information and date-and-time information are read, and moreover when the date-and-time information is within a valid period set in advance. That is, if the information from the IC chip 51 of the ignition key 50 satisfies the above conditions, when the driver performs the operation to start the engine 58, the engine control portion 57 performs startup of the engine 58. The above-described valid period may for example indicate validity only on the day of the decision to permit operation, or a time interval may be stipulated.

By means of the above-described fourth embodiment, information on the decision result of the permission decision portion 13 of the health state management device 10 is written by the RFID reader/writer 59 to the IC chip 51 held by the ignition key 50. The decision result information of the permission decision portion 13 written to this IC chip 51 is read by the RFID reader 56 of the transportation equipment 55, and if the read-out decision result information is permission information indicating a decision to permit operation of the transportation equipment 55, then the engine control portion 57 of the transportation equipment 55 executes control to enable startup of the engine 58 of the transportation equipment 55. Hence the engine 58 can be started only when the RFID reader 56 reads permission information from an ignition key 50 holding an IC chip 57 in which is stored permission information indicating a decision to permit operation of the transportation equipment 55.

As the conditions enabling startup of the engine, at least one among the above-described conditions may be adopted, or appropriate conditions may be combined.

In the health state management device 10, in addition to permission information indicating that permission to operate transportation equipment 55 and decision date-and-time information calculated from an internal clock, equipment identification information for the transportation equipment 55 which can be operated by the driver being judged and which is stored in association with the driver identification information for the driver being judged, may also be stored. In this case, when there is information within the equipment identification information stored in the IC chip 51 of the ignition key 50 which matches equipment identification information stored in advance in the engine control portion 57, and moreover when the permission information and date-and-time information are read out, and when the date-and-time information is within a valid period set in advance, the engine control portion 57 executes control so as to enable starting of the engine.

A configuration may be employed in which the above-described sensor portion 14 is further combined with a detection device to detect data not detectable by this sensor portion 14 (for example, the concentration of alcohol in the breath of the driver), and this data is included in making decisions as to whether to permit operation of transportation equipment.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A health state management device which manages information on a state of health of a driver of transportation equipment, comprising:
   an authentication portion which authenticates the driver;
   a health state judgment portion which measures blood component data of the driver authenticated by the authentication portion, and which judges the state of health of the driver using the blood component data, the blood component data including a predetermined specific item and a plurality of other items, wherein each of the predetermined specific item and the plurality of other items has a range of acceptable values;
   a decision portion which decides whether or not to permit operation of the transportation equipment based on a judgment result of the health state judgment portion; and
   a storage portion which stores the judgment result of the health state judgment portion and a decision result of the decision portion in association with driver identification information of the driver,
   wherein the decision portion decides not to permit operation of the transportation equipment when a value of the predetermined specific item is not within its range of acceptable values, and wherein the decision portion decides not to permit operation of the transportation equipment when a number of the other items having values within their ranges of acceptable values is smaller than a prescribed number.

2. The health state management device according to claim 1, wherein the authentication portion authenticates the driver by means of a vein pattern in a portion of a body of the driver.

3. The health state management device according to claim 1, wherein the health state judgment portion irradiates a portion of a body of the driver with infrared rays to obtain an absorption spectrum and analyzes the absorption spectrum to measure blood component data.

4. The health state management device according to claim 1, wherein
the authentication portion authenticates the driver by means of a vein pattern in a portion of a body of the driver,
the health state judgment portion irradiates a portion of a body of the driver with infrared rays to obtain an absorption spectrum and analyzes the absorption spectrum to measure blood component data, and
detection of the vein pattern used by the authentication portion and acquisition of the absorption spectrum used by the health state judgment portion are realized by means of a single sensor portion.

5. The health state management device according to claim 4, further comprising:
a key management portion which accommodates and manages a key to the transportation equipment; and
a control portion which, when operation of the transportation equipment is permitted by the decision portion, executes control to enable withdrawal of the key, accommodated by the key management portion, to the transportation equipment which can be operated by the driver, based on the driver identification information of the driver for whom the operation is permitted.

6. The health state management device according to claim 1, further comprising an output portion which outputs the decision result of the decision portion.

7. The health state management device according to claim 1, further comprising:
a key management portion which accommodates and manages a key to the transportation equipment; and
a control portion which, when operation of the transportation equipment is permitted by the decision portion, executes control to enable withdrawal of the key, accommodated by the key management portion, to the transportation equipment which can be operated by the driver, based on the driver identification information of the driver for whom the operation is permitted.

8. A health state management system comprising:
the health state management device according to claim 1;
a plurality of key managers which accommodate and manage keys including the key to the transportation equipment and which are connectable via a network to the health state management device; and
a control portion which, when operation of the transportation equipment is permitted by the decision portion, executes control to enable withdrawal of the key, accommodated by the key managers, to transportation equipment which can be operated by the driver, based on the driver identification information of the driver for whom the operation is permitted.

9. The health state management system according to claim 8, wherein
the authentication portion authenticates the driver by means of a vein pattern in a portion of a body of the driver,
the health state judgment portion irradiates a portion of a body of the driver with infrared rays to obtain an absorption spectrum and analyzes the absorption spectrum to measure blood component data, and
detection of the vein pattern used by the authentication portion and acquisition of the absorption spectrum used by the health state judgment portion are realized by means of a single sensor portion.

10. A health state management system comprising:
the health state management device according to claim 1;
the transportation equipment which receives prescribed data from an IC chip held in a holder;
a data writing portion which writes information on the decision result of the decision portion to the IC chip;
a data reading portion which reads the information on the decision result of the decision portion written to the IC chip; and
an engine control portion which executes control to enable starting of an engine of the transportation equipment when the information on the decision result read by the data reading portion is permission information which grants permission to operate the transportation equipment.

11. The health state management system according to claim 10, wherein
the authentication portion authenticates the driver by means of a vein pattern in a portion of a body of the driver,
the health state judgment portion irradiates a portion of a body of the driver with infrared rays to obtain an absorption spectrum and analyzes the absorption spectrum to measure blood component data, and
detection of the vein pattern used by the authentication portion and acquisition of the absorption spectrum used by the health state judgment portion are realized by means of a single sensor portion.

* * * * *